(12) United States Patent
Lattner et al.

(10) Patent No.: US 6,314,324 B1
(45) Date of Patent: Nov. 6, 2001

(54) VESTIBULAR STIMULATION SYSTEM AND METHOD

(75) Inventors: Stefanie Lattner, Gibsonia; Douglas M. Mechlenburg, Pittsburgh, both of PA (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/563,522

(22) Filed: May 3, 2000

Related U.S. Application Data

(60) Provisional application No. 60/132,627, filed on May 5, 1999.

(51) Int. Cl.[7] ............................................. A61N 1/00
(52) U.S. Cl. ................................. 607/42; 600/26
(58) Field of Search ................. 600/26–28; 607/1–3, 607/42, 72

(56) References Cited

U.S. PATENT DOCUMENTS

| | | | |
|---|---|---|---|
| 4,558,703 | 12/1985 | Mark | 607/42 |
| 4,667,676 | 5/1987 | Guinta | 607/42 |
| 5,591,216 | 1/1997 | Testerman et al. | 607/42 |
| 5,833,714 | 11/1998 | Loeb . | |
| 6,077,237 | 6/2000 | Campbell et al. . | |

OTHER PUBLICATIONS

Leob, Gerald Dr., The Bionic Neuron Article, 1996.

*Primary Examiner*—Jeffrey R. Jastrzab
(74) *Attorney, Agent, or Firm*—Michael W. Haas

(57) ABSTRACT

An apparatus and method in which the portions of the labyrinth associated with the labyrinthine sense and/or the nerves associated therewith are stimulated to perform at least one of the following functions: augment or control a patient's respiratory function, open the patient's airway, induce sleep, and/or counteract vertigo. In one embodiment, the vestibular stimulating system of the present invention includes 1) a stimulation element that performs the actual stimulation of the tissue, 2) a sensor to detect a physiological condition of the patient, and 3) a power/control unit that receives the signals provided by the sensor and causes stimulation energy to be provided to the stimulation element at an appropriate timing, level, pattern, and/or frequency to achieve the desired function. However, the present invention also contemplates eliminating the sensor in favor of applying a predetermined pattern of stimulation to the patient.

40 Claims, 6 Drawing Sheets

VESTIBULAR STIMULATION SYSTEM AND METHOD

CROSS-REFERENCE TO RELATED APPLICATIONS

This application claims priority under 35 U.S.C. § 119(e) from U.S. provisional patent application No. 60/1132,627 filed May 5, 1999.

BACKGROUND OF THE INVENTION

1. Field of the Invention

The present invention pertains to an apparatus and method of stimulating the vestibular system of a patient to provide a therapeutic benefit, and, in particular, to an apparatus and method in which the portions of the labyrinth associated with the labyrinthine sense and/or the nerves associated therewith are stimulated to perform at least one of the following functions: augment or control a patient's respiratory function, open the patient's airway, induce or promote sleep, counteract vertigo, or a combination of these functions.

2. Description of the Related Art

There are numerous techniques for providing respiratory assistance to a patient suffering from a respiratory disorder and/or dysfunction. For example, it is known to provide mechanical ventilatory assistance by delivering a flow of breathing gas to the patient's airway via a ventilator. This mechanical ventilation method of assisting the patient's respiratory effort has numerous disadvantages that are well documented. For example, the patient interface device, such as a tracheal tube, intubation tube and nasal/oral mask, can be difficult to place within or on the patient, may cause long-term problems in the patient, and/or may not be tolerated by the patient. In addition, because the mechanical ventilator replaces, either partially or completely, the respiratory effort of the patient, the patient may have difficulty being weaned off of the ventilator, especially if the patient has been using a ventilator for an extended period of time.

It is also known to provide ventilatory assistance to a patient by directly stimulating the patient's phrenic nerve, thereby causing the diaphragm to contract. It is also known to provide this so called "electroventilation" technique by placing electrodes on the chest of the patient to innervate the diaphragm or chest muscles directly. See, e.g., U.S. Pat. No. 4,827,935 to Geddes et al. entitled, "Demand Electroventilator." However, these conventional electroventilation techniques are relatively ineffective at imitating the natural respiratory function of the patient, because, in a normal patient, each respiratory effort involves a complex interaction of nerve and muscle stimulation that includes more tissues than just the phrenic nerve and diaphragm. Conventional electroventilation techniques target individual muscles or, at best, muscle groups, not the overall neuralmuscular systems that cooperate to produce a normal respiratory cycle.

There are also numerous techniques for maintaining airway patency and/or patient ventilation to treat sleep apnea syndrome. For example, a common technique for treating obstructive sleep apnea (OSA) is to provide the patient with a continuous positive airway pressure (CPAP) or a bi-level pressure that varies depending on whether the patient is in the inspiratory or expiratory phase of the respiratory cycle. The supply of gas to the patient provides a pneumatic splint for the portion of the airway that would otherwise collapse. It is also known to treat central sleep apnea (CSA) using a system similar to a non-invasive ventilator. Preferably, the CSA treatment system detects whether the patient has stopped breathing for a period of time that exceeds a predetermined threshold time period and provides ventilatory assistance if this occurs. These techniques for treating sleep apnea syndrome have disadvantages similar to those associated with providing ventilatory assistance to the patient; namely, some patients have difficulty tolerating the patient interface device. In addition, some patients have difficulty and/or are uncomfortable breathing against the flow of gas being delivered to their airway. Also, because these systems are used while the patient sleeps, they must be kept as quite as possible so as not to arouse the user or the user's sleep partner.

It is also known to treat OSA by electrically stimulating the musculature in the neck area associated with the upper airway. Relaxation of these muscles during sleep is believed to be a contributing, if not a primary, factor on the occurrence of OSA for many sufferers. One conventional method of electrically stimulating the muscles in the upper airway involves placing an electrode in direct contact with a surface of the patient and passing a current through the surface tissues to stimulate the underlying muscles. For example, an intraoral appliance has been developed that applies an electrical current within the oral cavity to induce contraction of the genioglossus muscle, thereby helping to maintain airway patency. Another known electrical stimulation appliance applies electrical energy to the exterior surface of the patient's neck below the chin to induce contraction of the underlying upper airway muscles.

Electromuscular stimulation using surface mounted electrodes creates relatively large current densities at the site of the electrodes. Because these current densities are disposed at the surface of the patient, which also typically contains a relatively large number of nerve endings, such electrical stimulation devices might, in some cases, cause unpleasant sensations, possibly arousing the user from sleep. In addition, some patients may not be comfortable wearing an electrical stimulation appliance either on their neck or in their mouth while they sleep.

It is also known to apply electrical stimulation directly to the nerves and/or muscles of the upper airway via electrodes implanted in the patient to induce tension in the muscles of the upper airway, thereby preventing them from collapsing during sleep. As with stimulating the phrenic nerve to induce respiration, these conventional neuralmuscular electrical stimulation techniques are relatively ineffective at imitating the natural upper airway muscle contraction function that takes place during normal breathing. Normal breathing involves a complex interaction of nerve and/or muscle stimulation that is precisely timed and is provided at precise stimulation levels so as to prevent airway collapse. Direct invasive, stimulation of the nerves and/or muscles associated with the upper airway targets one nerve/muscle specifically, and, therefore, does not reproduce the overall neuromuscular function of a normal human that is involved in maintaining airway patency during normal breathing. In addition, direct invasive stimulation of the nerves and/or muscles associated with the upper airway is considered to be relatively invasive medical procedure, and, therefore, may not be favored by a large number of patient's and/or caregivers.

It is also known to treat sleep apnea syndrome through surgical removal of tissues in the upper airway. In addition, pharmacological solutions have also been pursued, at least with respect to the treatment of central sleep apnea. However, neither of these therapies is successful in all cases.

Surgical removal of tissue is invasive, introduces a potential for complications, the long term effects are not known, and is only marginally successful. Pharmacological therapy has been, in general, less than satisfactory, and side effects are frequent.

There are many patients that suffer from sleeping disorders in addition to or other than sleep apnea syndrome. For example, many people have difficulty falling asleep. Although the specific pathological reasons why some people have difficulty falling asleep are not believed to be known, many phramacological solutions exist for assisting a person to fall asleep. However, such medications, which are essentially relaxants, may not be appropriate for some people, due to undesirable, known, or unknown drug interactions, for example, and, therefore, are disfavored by some patients and/or caregivers. In addition, these medications may produce undesirable side effects, such as excessive drowsiness. More seriously, these medications may be contraindicated, and, therefore, a health risk.

It is also known that physically rocking the patient can be helpful in inducing sleep. To this end, beds with mechanical rocking mechanisms have been developed. It can be appreciated, however, that the rocking motion may not be tolerated by the patient's bed partner. In addition, providing a bed that can rock an adult requires relatively costly, mechanically complicated, and potentially noisy rocking mechanisms to move the bed in the desired rocking direction. In addition, such rocking beds are typically cumbersome, aesthetically displeasing and not practical in many homes.

Although not related to respiration or sleep, another disjunction of interest with respect to the present invention is vertigo and/or dizziness, which are disorders in which the sufferer has the sensation that they or their surroundings are whirling. These disorders may be induced by pathological reasons or from the physical movement of the user, such as spinning in a disorienting fashion. Vertigo, for example, may also be the result of an inner ear disorder that effects the patient's balance system. Depending on the underlying cause, treatment of these disorders include physical therapy, cranial manipulation, surgery, and pharmacological intervention. However, some causes of vertigo and/or dizziness have no cure or treatment. Furthermore, the existing physical therapies, cranial manipulation treatments, and surgeries are time consuming, may be only moderately effective, or are only effective for specific types of diseases. Pharmacological treatments can produce undesirable side effects and may not provide immediate relief.

SUMMARY OF THE INVENTION

Accordingly, it is an object of the present invention to provide a system that performs one or more of the following: augment or control a patient's respiratory function, open the patient's airway, induce sleep, and/or counteract vertigo that overcomes the shortcomings of conventional treatment techniques. This general object is achieved according to principles of the present invention by providing a vestibular stimulation system that stimulates at least a portion of the labyrinth associated with the labyrinthine sense and/or at least one of the nerves in the inner ear associated with the labyrinthine sense, such as the vestibular nerve and the branch nerves associated therewith. The general configuration for a vestibular stimulation system that accomplishes this object includes a stimulation element that stimulates the targeted tissue, a stimulation power supply and control system that provides and controls the application of stimulation energy to the targeted tissue via the stimulation device, and, in some applications, an input device, such as sensor, for providing input data to the control system so that the control system can determine when and how to apply stimulation energy to the patient via the stimulation element. Configurations for the stimulation system that performs the above identified physiological functions are described briefly below.

Augmenting or controlling a patient's natural respiratory function is accomplished by stimulating the vestibular nerve and/or one or more nerve branches associated with the vestibular nerve, either directly or indirectly, so as to induce a neural transmission in the vestibular nerve. Because of the interaction between the vestibular nerve and the nerves associated with respiration, such as the phrenic, hypoglossal, and recurrent laryngeal nerves, stimulation induced in the vestibular nerve induces stimulation in the nerves associated with respiration to cause or assist the patient in breathing. By inducing a neural transmission in the vestibular nerve, the vestibular stimulation system can be used to control one or more parameters associated with the patient's respiration, such as set the start of inspiration, the duration and/or the force of the respiratory effort. For a patient that has compromised respiratory effort, stimulating the vestibular system can be used to assist the patient's ventilation. If the patient is breathing on their own, but not at an adequate level, stimulating the vestibular system can augment the patient's natural respiratory function to increase the patient's respiratory effort. In one embodiment, the present invention contemplates using at least one sensor and a control algorithm or algorithms to synchronize triggering of the vestibular stimulation with the patient's respiratory cycle. However, the present invention also contemplates providing a time varying stimulation energy to at least a portion of the vestibular system irrespective of the patient's respiratory cycle. In which case, the patient will synchronize his or her respiratory cycle with this stimulation cycle.

Because stimulation of the vestibular nerve elicits stimulation in the hypoglossal, and recurrent laryngeal nerves, stimulating the vestibular system can also be used to maintain airway patency to treat OSA and upper airway resistance syndrome. Preferably, a sensor detects the patient's respiratory cycle, such as by monitoring respiration, and the control system applies stimulation to the vestibular system at an appropriate time, duration, and pattern during the respiratory cycle to maintain the patency of the patient's airway.

Inducing or augmenting sleep is accomplished by rhythmically stimulating the semicircular canal, saccule, utrical and/or ampullae, or the nerve branches associated with these structures, to produce a uniform rocking sensation in the patient. For example, locations on one or more of the semicircular canal(s), saccules, and/or utricles can be stimulated so as to cause a back and forth flow of the fluid in the semicircular canal to create the rocking sensation. This artificially created rocking sensation, like the actual rocking provided by a physically rocking the patient's bed, helps the patient relax and eventually fall asleep, as well as promotes sleep once the patient has fallen asleep.

Countering vertigo and/or dizziness is accomplished by stimulating the vestibular system in a manner to as to mask out the signals from the vestibular system that would otherwise be interpreted by the brain as a spinning sensation. Preferably, a sensor detects the motion of the patient and/or the unusual activity from the nerves in the inner ear and causes the vestibular stimulation system of the present invention to compensate for this motion and/or unusual neural activity by stimulating the vestibular system in such a manner so as to mask out the signals indicative of spinning and/or the unusual neural signals. Thus, stimulating the vestibular system only takes place when the signals from the vestibular system would be interpreted by the brain as a spinning sensation and/or when the signals from the vestibular system are not normal, which, if not treated, may cause the patient to experience vertigo.

It is yet another object of the present invention to provide a method of augmenting or controlling a patient's respiratory function, opening the patient's airway, inducing sleep, and/or counteracting vertigo that does not suffer from the disadvantages associated with conventional techniques for accomplishing these functions. This object is achieved by providing a method that includes providing stimulation to the receptors of the labyrinth associated with the labyrinthine sense and/or the nerves associated with such receptors, including the vestibular nerve and its branches.

For the method of augmenting or controlling a patient's respiratory function and opening the patient's airway, this process, in one embodiment of the present invention, includes sensing the condition of the patient, such as his or her respiratory cycle, and synchronizing the stimulation with the inspiratory phase in the case of augmenting the respiratory function. In another embodiment, a time varying stimulation energy is applied to at least a portion of the vestibular system irrespective of the patient's respiratory cycle, with the patient naturally synchronizing himself or herself to this stimulation cycle. In addition, for opening the patient's airway, the method can include determining when conditions of the patient suggest that airway closing or cessation of breathing will occur and only provide vestibular stimulation if such conditions are present. For example, the stimulation system can detect when the patient is asleep, lying down, ceases breathing, or snores and begin the stimulation therapy only when one or more such conditions exist.

For the method of inducing or promoting sleep, this stimulation process can include applying stimulation to one or more of the semicircular canals, ampullae, saccule and/or utricle so as to produce a rocking sensation in the patient. In addition, this method can include sensing when the patient is in a preferred body position, such as supine, and/or sensing whether the patient is asleep or awake so that stimulation to produce the rocking sensation is only initiated if the patient is supine and awake, for example. This method can also include providing the stimulation for a set duration, such as a predetermined period of time, following initiation of the stimulation therapy so that the stimulation is applied to put the patient to sleep, but discontinues some time later, preferably once the patient has fallen asleep, much the same way a sleep timer on a radio or television functions to turn of the appliance after a set period of time. Of course, the stimulation process can also continue throughout the sleep duration because the rocking sensation is believed to promote a restful sleep for the patient even after the patient has fallen asleep.

For the method of counteracting vertigo, the vestibular stimulation process includes applying stimulation to the vestibular system in such a manner so as to mask out the signals from the semicircular canals that would otherwise be interpreted by the brain as a spinning sensation. In addition, this method can include sensing the motion of the patient so that the masking stimulation is only applied if the patient is actually in motion.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
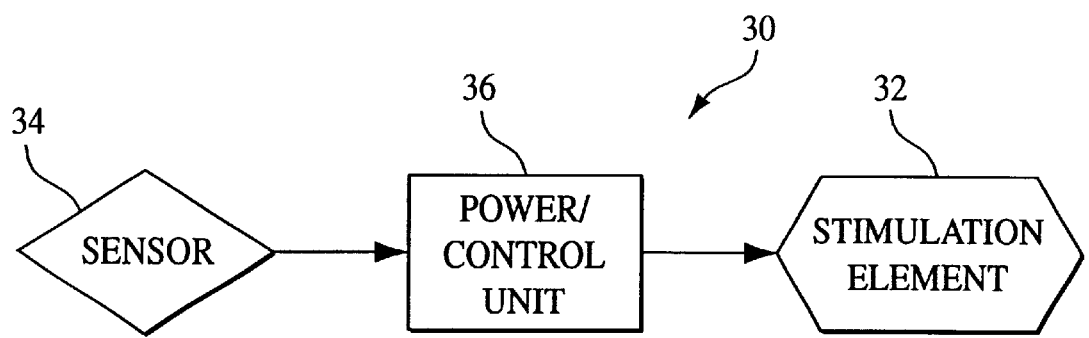
FIG. 1 is a schematic diagram of a vestibular stimulation system according to the principles of the present invention.

FIG. 1 schematically illustrates an exemplary embodiment of a vestibular stimulating system 30 according to the principles of the present invention. Vestibular stimulating system 30 is a device that stimulates portions of the labyrinth associated with the labyrinthine sense and/or associated nerves to provide a therapeutic benefit to the patient. More specifically, the present invention contemplates stimulating, either invasively or non-invasively, the receptors of the labyrinth associated with the labyrinthine sense and/or the nerves or nerve branches associated with such receptors, including the vestibular nerve and its nerve branches. The present invention contemplates providing stimulation to at least one of these stimulation sites to perform one or more of the following functions: a) augment or assist a patient's natural respiratory function, b) open the patient's airway, c) induce or promote sleep, and d) counteract vertigo. The details of the particular sites of stimulation and the preferred stimulation mechanisms to achieve each of these functions are described below. However, a general description of the stimulation system of the present invention is first provided. It should be noted that the stimulation system of the present invention is referred to through the present disclosure as a "vestibular stimulation system" because the simulation sites of interest in the present invention are the above-identified structures and/or tissues of the human inner ear associated with the labyrinthine sense, which is commonly referred to as the vestibular system.

As shown in FIG. 1, vestibular stimulating system 30 includes the following three components: a stimulation element 32 that performs the actual stimulation of the tissue, a sensor 34 to detect a physiological condition of the patient, and a power/control unit 36 that receives the signals provided by sensor 34 and causes stimulation energy to be provided to stimulation element 32 at an appropriate timing, level, pattern, and/or frequency to achieve the desired physiological function. As will become apparent, there may be instances where sensing a physiological condition of the patient is not necessary in order to deliver the appropriate stimulation. For example, in one embodiment of the present invention, the stimulating system provides stimulation to the patient regardless of the patient's condition or respiratory state. In which case, the sensor can be eliminated or simplified to an on/off switch that activates and deactivates the supply of stimulation energy via the power/control unit.

Stimulation element 32 is any device or combination of devices that provides a controlled stimulation to a target site. As noted above, the particular stimulation sites of interest in the present invention are one or more of the following and/or a combination thereof: the vestibular nerve, portions of the vestibular nerve, the branches of vestibular nerve or portions thereof, each of the semicircular canals (anterior, posterior, and lateral) or portions thereof, the common limb, utricle, saccule, and ampullae. It is to be understood that the precise stimulation site or sites, as well at the method in which the sites are stimulated, will vary depending on the physiological function to be achieved. Stimulation of each of these tissues can be provided on the surface, internally, or in nearby tissues or structures. In addition, depending on the stimulation technique used, the stimulation devices can be completely invasive, completely non-invasive, or a combination thereof.

The present invention contemplates stimulating one or more of the above stimulation sites using one or more of a variety of stimulation techniques, such as electrical, mechanical, magnetic, thermal or chemical stimulation. The specific mechanism or combination of mechanisms for delivering the stimulation will depend on the stimulation technique used, which will depend on the stimulation site selected. The following are examples of suitable stimulation techniques and their stimulation mechanism that can be used in the vestibular stimulation system of the present invention to stimulate one or more of the stimulation sites identified above:

1) Electrical Stimulation—The present invention contemplates providing electrically conductive electrodes in, on, and/or near the tissue to be stimulated so that an electric current can be delivered to the adjacent tissue via the electrode. The electrode or electrodes can have a variety of sizes and configurations depending on the stimulation pattern to be provided. For example, a point electrode can be used to stimulate a very specific site, or a spot or strip electrode can be provided to induce stimulation over a larger area. In addition, the present invention contemplates using a microstimulator electrode that is inserted at the stimulation site and that receives power and control data from an external source, such as an rf field created by an external oscillator.

A specific type of a strip electrode that can be used in the present invention to stimulate a nerve is an electrode cuff that completely or partially surrounds a nerve or nerve branch to be stimulated. Because the cuff surrounds to target nerve, it allows the stimulation energy to be delivered through the nerve tissue while minimizing collateral stimulation of other tissues. Of course, multiple electrodes and electrode pairs can be provided to achieve the desired stimulation pattern over the desired area to be stimulated. In addition, the present invention contemplates inserting one or more needle electrodes into the inner ear for selective simulation of a nerve, nerve branch, or a global area, such as the saccule, to promote the desired physiological effect. A needle electrode has the advantage of being able to target a specific location for stimulation.

2) Mechanical Stimulation—The present invention contemplates placing a pressure application device, such as an inflatable balloon, near the tissue to be stimulated so that inflating the balloon applies a pressure on the adjacent tissue. This type of mechanical stimulation system provides pressure fluctuations to the patient to promote a particular sensation. Another example of a pressure application device particularly well suited for use with the semicircular canal or with a nerve is a pressure cuff, which is placed either completely or partially around the canal or nerve to be stimulated so that inflating the pressure cuff exerts pressure on the underlying portion of the semicircular canal or nerve. Yet another mechanical stimulation device is a vibrating element that produces a mechanical vibration at a selected frequency.

3) Sonic Stimulation—The present invention also contemplates stimulating the vestibular area or specific sites within this area using a sonic or ultrasonic device that delivers stimulation on a carrier wave typically above 20,000 Hz, which is not in the audible range for humans.

4) Magnetic Stimulation—The present invention further contemplates providing a magnetic field generator in the form of one or more coils in and/or near the inner ear. The coils generate a time varying magnetic field that created a spatially varying electric field that induces stimulation in the target tissue. In addition, focusing elements, such as ferromagnetic material implants, can be provided in or near the targeted tissue to focus or shape the magnetic field, and, hence the electric field, at a specific location.

5) Thermal Stimulation—The present invention contemplates providing a stimulation device that uses changes in temperature to induce stimulation of the patient's tissue. Examples of devices that an induce a temperature change include a laser, infrared device, or a device that dispenses heated or chilled liquid to the stimulation site.

6) Chemical Stimulation—The present invention further contemplates providing a device that introduces chemicals or that causes chemical reactions at a stimulation site to control the stimulation at that site. For example, an injection or medicine pump can be provided at the inner ear to introduce the desired stimulation medication at the stimulation site.

7) Radio-Frequency Stimulation—The present invention still further contemplates using radio frequency wavelengths generated by a suitable device to provide the desired stimulation. For example, as noted above, stimulation can be induced by providing power and control data using radio frequencies (rf) received by one or more microstimulators implanted in the patient. Different microstimulators implanted at different locations in the patient can be tuned to different frequencies so that a wide variety of stimulation patterns can be achieved.

8) Infrared Stimulation—The present invention also contemplates using infrared technology to deliver the stimulation to the patient's tissues. Short wave, 7,200–15,000Å, or long wave, 15,000–150,000Å, systems can be used to deliver the stimulation to the target site.

It is to be understood that this list of stimulation techniques is not exhaustive or exclusive. On the contrary, the present invention contemplates using any stimulation technique or device that, when actuated, provides the desired stimulation function. The selection and different types of suitable stimulation devices suitable for use in achieving the desired physiological function of the present invention will be better understood from the discussion of the particular implementations of the stimulation system of the present invention provided below.

Sensor 34 is a device that detects a physiological condition of the patient or the external conditions that the patient is experiencing and provides this information to power/control unit 36. It can be appreciated that the specific type of sensor used with the stimulation system of the present invention to monitor one or more of these parameters will depend on the parameter of interest. Nevertheless, examples of suitable sensors for use with the present invention include: 1) a pressure sensor that detects a pressure of a fluid, 2) a flow sensor that detects a flow of a fluid, 3) an effort sensor that detect expansion and contraction of the thorax, 4) an oximeter, 5) a temperature sensor, 6) a microphone, 7) a nerve activity or conduction sensor, 8) an EMG sensor, 9) an EEG sensor, 10) an EOG sensor, and 11) an accelerometer. Details of how each of these sensor is optimally used in conjunction with the vestibular stimulation system of the present invention are provided below.

It is to be understood that this list of suitable sensors is also not exhaustive or exclusive. On the contrary, the present invention contemplates using any sensor that is capable of detecting or monitoring a characteristic of the patient of interest, such as the patient's respiratory cycle, and that provides a signal indicative thereof. As with stimulation element 32, the selection and different types of suitable sensors for use with each embodiment of the present invention can be appreciated from the discussions of the particular implementations of the stimulation system of the present invention.

Power/control unit 36 is any device that provides stimulation energy to the patient via the stimulation element and that is capable of controlling the application of this energy. For example, power/control unit 36, is, in one embodiment of the present invention, a rechargeable battery with a pulse shaping device that modulates the shape, frequency and amplitude of pulses of stimulation energy provided to the stimulation element by the battery. The power/control device preferably also includes a processor that is capable of receiving signals from sensor 34 and controlling the application of stimulation energy, i.e., the shape, time, frequency, and/or amplitude of the pulses applied to the stimulation element, based on the input signals from sensor 34 to achieve the desired physiological function. Of course, if sensor 34 is eliminated, the power/control device provides the stimulation energy according to predetermined criteria.

The present invention contemplates that power/control unit 36 can include an "intelligence" capability that provides relatively complex control functions, such as adaptively controlling the stimulation energy, compensating for changes in monitored parameters, allowing the user to specify the control ranges, and detecting between events of interest, such as respiration and snoring, and noise. For example, in an exemplary embodiment of the present invention, the user or manufacturer provides the power/control unit with the stimulation parameters, such as intensity, frequency, interpulse duration, for the stimulation energy to be provided to the patient. Thereafter, these parameters are changeable by the patient or adaptively changeable by the control unit so that the target nerve firing rate is controllable to create the desired stimulation function.

A variety of control techniques can be used to provide this intelligent capability, such as fixed parameter control where the control unit causes a certain action if a particular parameter is detected, threshold based control where the control unit compares an input signal to a threshold to determine if an action is required, rule based control, fuzzy logic, and neural network control. Power/control unit 36 can be provided outside the patient, entirely within the patient, or a combination thereof. Details of the function of the power/control unit to control the stimulation energy provided to the patient and specific examples of this device are discussed below.

Figure 2:
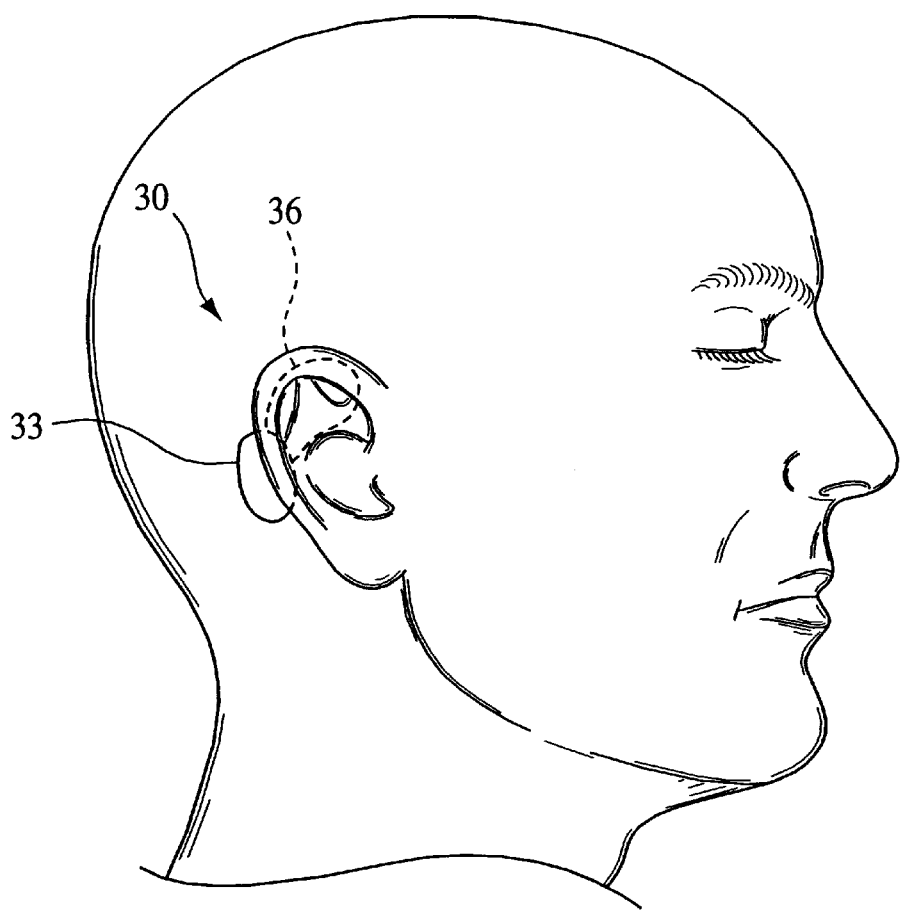
FIG. 2 is a side view of a human head showing the positioning of a vestibular stimulation system using surface electrodes as a stimulating element according to one embodiment of the present invention.
Figure 3:
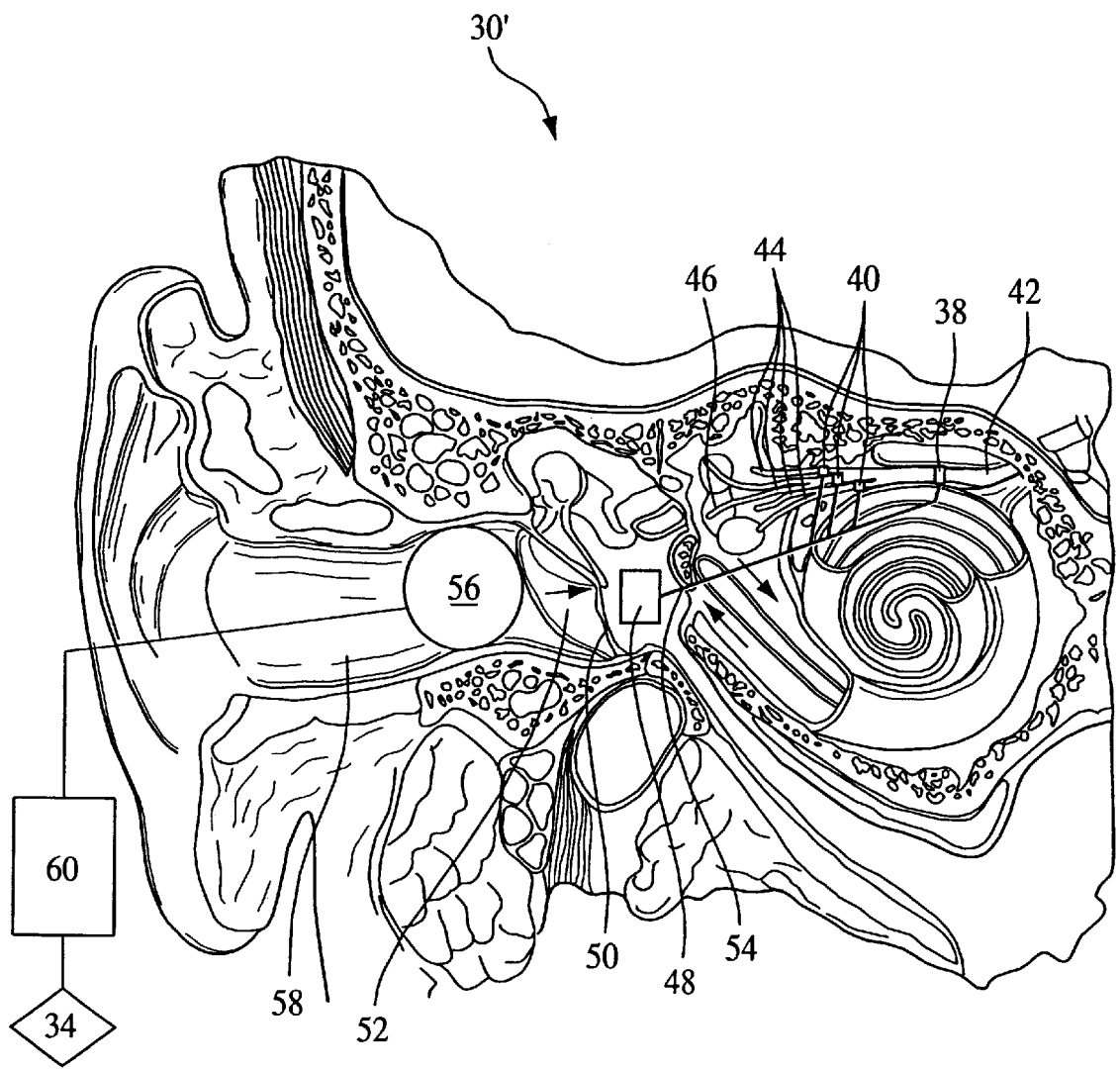
FIG. 3 is a sectional view of a portion of the human anatomy showing the inner ear and schematically showing a vestibular stimulation system according to one embodiment of the present invention.
Figure 4:
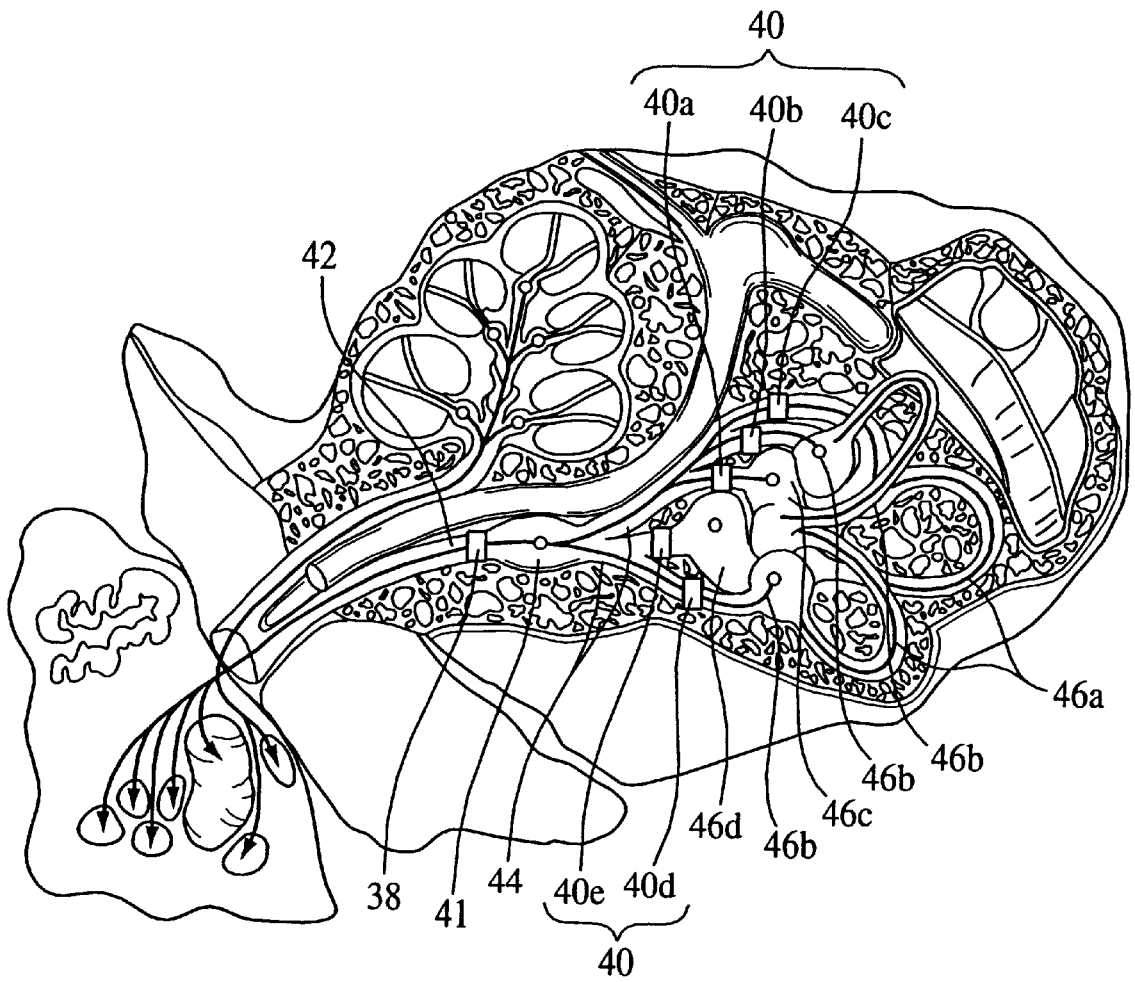
FIG. 4 is a sectional view of a portion of the human anatomy also showing the inner ear and schematically showing the location of stimulation electrodes on the vestibular nerve and nerve branches.

FIGS. 2, 3 and 4 illustrate exemplary embodiments of vestibular stimulation systems 30. In FIG. 2, vestibular stimulation 30 is a completely non-invasive system in that no part of the system is disposed in the patient. Vestibular stimulation system 30 in FIG. 2 includes a stimulation element 33 in the form of a surface electrode that is disposed on the surface of the patient just behind the ear so that the electrode generally overlies the vestibular system. The remaining portions of the stimulation system, such as the power supply and the control unit 36, are worn on the ear in the same manner as a conventional hearing aid. When activated, the power supply and control unit 36 energize electrode 33 to send a stimulating current to the patient's vestibular system.

In FIG. 3, vestibular stimulation system 30' is an invasive system that directly stimulates the vestibular nerve and/or its branches. Vestibular stimulation system 30' of FIG. 3 includes stimulation elements 38 and 40, which are electrodes placed directly on or near vestibular nerve 42 and branch nerves 44 that lead to the vestibular nerve. The present invention contemplates that electrodes 38 and/or 40 can be positioned relative to the vestibular nerve 38 and/or a branch nerves 44 associated therewith, respectively, at a variety of locations along these nerves or nerve branches, so long as they are positioned so as to induce stimulation in the associated nerve. For example, electrode 38 can be provided on vestibular ganglion 41. Branch nerves 44 are the nerves coupled to the receptors of the labyrinth associated with the labyrinthine sense, such as the semicircular canals 46a, ampullae 46b, utricle 46c, and saccule 46d. Note that the semicircular canals, ampullae, utricle, and saccule are generally identified by numeral 46 in FIG. 3, but are shown in greater detail in FIG. 4. Branch nerves 44 combine to form vestibular nerve 42.

FIG. 4 illustrates in better detail the inner ear and the placement of electrodes 41a–41e on branch nerves 44 and the placement of electrode 38 on vestibular nerve 42. Electrodes 41a–41e are generally illustrated in FIG. 3 as electrodes 40. It is to be understood that the number of electrodes and their locations can vary and that electrode stimulators need not be placed on each branch nerve. For example, electrode 38 on vestibular nerve 42 or one or more electrodes 41a–41e on branch nerves 44 may be eliminated if the desired stimulation effect is achieved by stimulating another nerve or nerves. Ideally, the number of electrodes should be kept to a minimum while providing the desired stimulation effect.

Referring again to FIG. 3, in the illustrated exemplary embodiment, power/control unit 36 of vestibular stimulation systems 30' includes a signal receiving device 48 implanted in tympanic cavity 50 on the interior side of eardrum 52. A signal generator 56 is provided on the exterior side of eardrum 52 in ear canal 58. One or more leads 54 couple signal receiving device 48 to each of electrodes 38 and/or 40 so that each electrode can be energized individually or in any combination. For example, this configuration allows for simultaneous stimulation of multiple electrodes at multiple sites based on a common stimulation source from signal receiving device 48. In addition, this configuration allows for independent control of one or more of the electrodes to provide a great degree of flexibility for the different types of stimulation patterns that can be applied to the patient's vestibular system. For example, the present invention contemplates stimulating between sites, for example, from 41a to 41b, 41a to 41c, 41b to 41c, etc.

Signal generator 56 communicates with signal receiver 48 to cause signal receiver to provide stimulation energy to stimulation electrodes 38 and/or 40. In an exemplary embodiment of the present invention, signal generator 56 generates an electro-magnetic field that induces a current in signal receiving device 48, which is then transmitted to electrodes 38 and/or 40. If, however, signal receiving device 48 is provided with its own power supply, the signals from signal generator 56 are command and control signals that dictate how and when the stimulation energy is output from signal receiving device 48. It should be noted that signal generator 56 need not be provided within the ear canal, as shown, if its transmission range is sufficient to transmit greater distances.

The present invention also contemplates doing away with signal receiving device 48 and leads 54 in favor of having an electromagnetic field produced by signal generator 56 directly induce stimulation pulses at the electrodes or at the stimulation site. For example, magnetic stimulation can be used to induce stimulation in the target tissue. In which case, the coil or coils that generate the magnetic field function as signal generator 56, and electrodes 38 and/or 40 can be eliminated. Alternatively, ferromagnetic devices that shape the fields generated by the can be provided at or near the stimulation sites to function in much the same capacity as electrodes 38 and/or 40 to ensure that the target site is adequately and properly stimulated.

The present invention also contemplates that one or more microstimulators, which receive power and data from an external source via rf frequencies, can be implanted in the patient to function as electrodes 38 and/or 40. In which case, the rf oscillator functions as signal generator 56 and is located externally relative to the patient, such as at the patient's bedside.

A power/control unit 60, similar if not identical in function to power/control unit 36 discussed above, causes signal generator 56 to produce the electro-magnetic field or other coupling mechanism that initiates stimulation. In the illustrated embodiment, at least one sensor 34 communicates with power/control unit 60 to provide an input signal that is used by the control unit to determine when to generate the electro-magnetic field. As discussed in greater detail below, the specific type of sensor or sensors used, and how the control unit uses the received signals to provide stimulation energy to the stimulation elements 38 and/or 40 will depend on the physiological function to be achieved as a result of the stimulation of the vestibular system. Power/control unit 60 is preferably provided outside the patient to simplify recharging or replacing the power supply. Sensor 34 is also typically provided outside the patient. However, sensor 34 may be implanted within the patient if the parameter being monitored requires and/or allows for an invasive location for the sensor.

As noted above, the present invention contemplates stimulating one or more locations in the inner ear associated with the labyrinthine sense, in addition to or in place of direct stimulation of the vestibular nerve and its branches, as shown in FIGS. 2, 3 and 4, in order to provide a therapeutic benefit. That is, it is not necessary that the vestibular nerve or its branches be directly stimulated in order to induce a neural transmission in the vestibular nerve. Because the vestibular nerve is an afferent nerve, and stimulating anything before it involves transduction, stimulation can be provided at one or more sites before the vestibular nerve and still induce the desired neural transmission therein. It should be noted that the term "before" as used in this paragraph refers to portions of the nerve in a direction opposite the direction of normal neural conduction.

Figure 5:
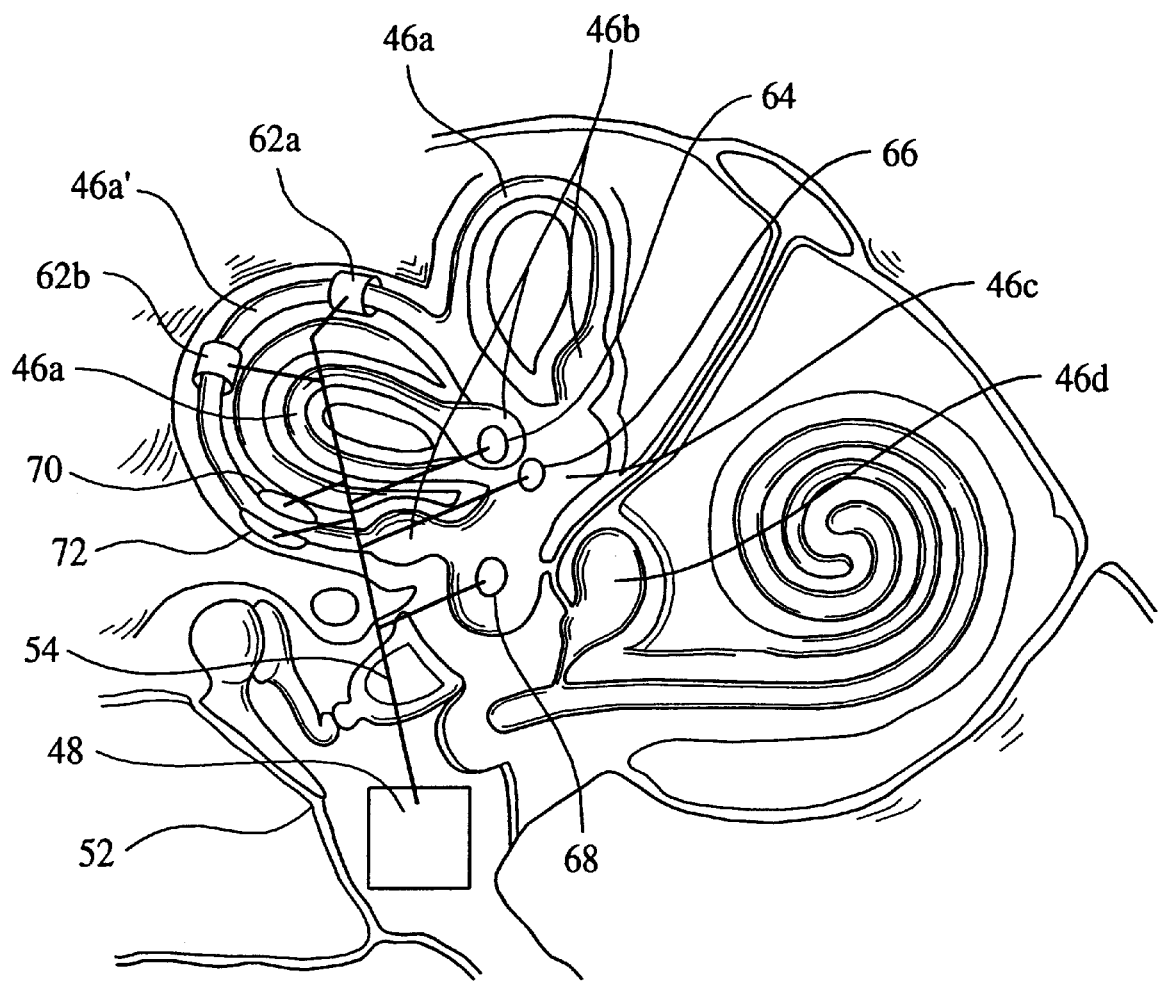
FIG. 5 illustrates a portion of the inner ear showing additional stimulation sites and stimulation elements.

FIG. 5 illustrates a portion of the inner ear showing additional stimulation sites that, once stimulated, induce a neural transmission in the vestibular nerve to provide a therapeutic benefit to the patient. The basic components of the stimulation system shown in FIG. 5 are the same as those illustrated in FIGS. 2–4 except for the stimulation sites. For the sake of illustration, a variety of stimulation devices serving as stimulation element 32 are shown in this embodiment of the present invention. For example, FIG. 5 illustrates a pair of cuffs 62a and 62b spaced apart from one another and each surrounding a portion of the posterior semicircular canal 46a'. Cuffs 62a and 62b can be electrodes or pressure application devices that exert a force on the semicircular canal. In addition, FIG. 4 illustrates electrodes or pressure application devices 64, 66 and 68 provided on an ampulla 46b, and portions of utricle 46c for stimulating these structures. In addition, FIG. 5 illustrates electrodes or pressure application devices 70 and 72 provided on either side of posterior semicircular canal 46a'. It is to be understood that the present invention contemplates stimulating the outside of the semicircular canals, as shown, as well as stimulating within the semicircular canals. Lead or leads 54 couple signal receiving device 48 to each of these stimulation elements to provide the appropriate stimulation energy or impetus, such as a current in the case of an electrode or an inflating fluid in the case of a pressure application device.

The configuration for vestibular stimulation system 30, 30' shown in FIGS. 2–5 is advantageous in that it minimizes the number and complexity of components that are provided within the patient. It is to be understood that the present invention contemplates that the power supply could include one or more miniature batteries implanted within the patient, rather than the current coupling system shown in the figures. Such an implanted battery system, however, increases the amount of foreign objects that must be disposed within the patient. In addition, if it became necessary to replace the batteries at some point in the future, an additional surgery would be required.

The configuration for vestibular stimulation system 30, 30' shown in FIGS. 2–5 is further advantageous in that no elements of the system are penetrating the patient's tissues from an internal to external location. It is to be understood that the present invention contemplates eliminating signal receiving device 48 and extending leads 54 outside the body, such as through the eardrum or through the surrounding tissue, for providing energy to the electrodes. Alternatively, the present invention contemplates that electrodes 38 and/or 40 are relatively stiff needle electrodes that insert through the eardrum, for example, with the distal end remaining outside the patient. In these configurations, leads or electrodes must physically pass from an interior location within the patient to an exterior location so that they can be coupled to the power/control unit. While this embodiment provides a good path of conduction for the stimulation energy and minimizes the amount of foreign objects located within the patient, when a foreign object extends through the patient's tissue, providing a path from the interior to the exterior of the patient, this represents a potential site for infection or provides a pathway by which infections may enter the body.

While FIGS. 2, 3, and 4 illustrate an electrode stimulation system, it is to be understood that any of the above-described stimulation techniques can be employed to stimulate the patient's vestibular system. For example, electrodes 38 and/or 40 can be replaced with pressure cuffs to apply a physical pressure on the vestibular sensory tissue. As will be understood from the following discussions of the physiological functions that can be achieved by the stimulation system of the present invention, the present invention contemplates stimulating sites within the inner ear other than or in addition to the nerve stimulation sites shown in FIGS. 2, 3, and 4. For example, the same stimulation effect accomplished by stimulating the vestibular nerve directly may be accomplished by globally stimulating the portions of the labyrinth associated with the labyrinthine sense. Please refer to FIG. 5 for a discussion of other exemplary stimulation sites of the present invention.

Augmenting and/or Controlling A Patient's Respiratory Function

In one embodiment of the present invention, vestibular stimulation system 30, 30' is used to accomplish the physiological function of augmenting the respiratory effort of a patient. This is accomplished by stimulating the vestibular nerve either directly, as shown in FIGS. 3 and 4, or indirectly, as shown in FIGS. 2 and 5, in synchronization with the patient's respiratory cycle. Details of this embodiment are discussed below with reference to FIGS. 2–7.

As noted above, vestibular nerve 42 is connected polysynaptically to the phrenic nerve, abdominal nerve, hypoglossal nerve, and the recurrent laryngeal nerve, all of which are associated with the musculature of the respiratory system. For this reason, stimulating the vestibular nerve has the effect of stimulating, on a macro level, all of these other respiratory-related nerves. This, in turn, induces or augments the contraction of the respiratory muscles, thereby supporting or augmenting the overall respiratory function of the patient. By varying the stimulation level of the vestibular system, the present invention can control the degree of ventilatory assistance provided to the patient.

As noted above, stimulating the vestibular system in this manner provides a macro stimulation of many, if not all, of the respiratory muscles, such as the diaphragm and intercostal muscles, while targeting the stimulation at a relatively small site. Conventional electroventilation systems, on the other hand, target the phrenic nerve, portions of the phrenic, or the respiratory muscles directly, see, e.g., U.S. Pat. No. 4,827,935 and the article by Geddes et al. entitled, "Electrically Produced Artificial Ventilation" published in 1988 at pages 263–271 in vol. 22, no. 6, of a periodical entitled Medical Instrumentation. As a result, these electroventilation techniques provide only a micro-stimulation of one component of the overall physiology associated with providing a respiratory effort.

In one embodiment of the present invention, the application of the stimulation energy to the vestibular system is synchronized with the patient's respiratory cycle. In this embodiment, sensor 34 in vestibular stimulation system 30, 30' is any device, apparatus or system that is capable of detecting and/or monitoring the respiratory cycles of a spontaneously breathing patient and that can be used to discern between the inspiratory and the expiratory phases of the respiratory cycle. For example, the present invention contemplates detecting the flow, pressure, or volume of fluids delivered to or inspired by the patient during breathing. Detecting these parameters associated with the patient's breathing can be accomplished, for example, using a pneumotach flow meter in communication with the patient's airway. This information can then be processed by control unit 60 using well known techniques to determine the phase of the respiratory cycle.

The present invention also contemplates detecting sounds of the patient's breathing to discern when the patient is breathing in and out. In addition, the present invention contemplates detecting patient movement, such as the rise and fall of the chest, via sensor 34 to detect the inspiratory and the expiratory phases of the respiratory cycle. Numerous techniques, such as resistance or inductance belts, pressure sensors, and impedance pneumography, are known for detecting such movement of the patient. Other suitable sensors that detect patient respiration include a temperature detecting system that detects temperature variations associated with a patient's respiration. For example, it is known to provide a thermister at or near the patient's airway to detect the heat associated with the expired air from the patient. Thus, when heat is detect by such a sensor, this indicates that the patient as reached the expiratory phase of the respiratory cycle. See, for example, U.S. Pat. Nos. 5,190,048 and 5,413,111 both to Wilkinson, the contents of which are incorporated herein by reference. In addition, sensor 34 in this embodiment can detect the electrical/neural activity of a patient associated with a patient's respiration, such as the EMG signal from the diaphragm to detect inspiration and expiration.

In this embodiment, stimulation is provided to the vestibular system in synchronization with the patient's breathing, so that stimulation of vestibular nerve 42 occurs at an appropriate time to coincide with the onset of an inspiration, thereby augmenting the patient's natural breathing. It can be appreciated that synchronizing the stimulation with the patient's inspiration may require initiating the process of providing stimulating energy prior to the commencement of the inspiratory phase to account for any time lag introduced by the stimulation system and any physiological lag time, such as the time it may take for the stimulation energy to induce a stimulation in the target tissue and the time it may take for the excitation of the vestibular nerve to travel to the portions of the body, such as the brainstem, where it induces a stimulation in the nerves associated with respiration.

In another embodiment of the present invention, stimulation of the at least a portion of the vestibular system is provided irrespective of the patient's own respiratory cycle or efforts. Instead, stimulation energy is applied continuously in a time varying fashion, such as in the form of a sine wave. The patient will naturally synchronizing their own respiratory cycle with that of the stimulation cycle. This represents a significant simplification over a stimulation system that attempts to synchronize the application of stimulation with the patient's respiratory cycle, in that sensor 34 and its feedback functions are eliminated. Yet, this embodiment of the present invention effectively accomplishes the respiration augmentation or control function, because the patient will naturally adjust their own respiratory pattern to match the stimulation pattern being applied to the vestibular system by the vestibular stimulation system.

In an exemplary configuration for this embodiment of the present invention, stimulation is provided directly to vestibular nerve 42 and/or to the branch nerves 44. See FIGS. 3 and 4, which illustrate a system for stimulating these nerves. FIG. 5 also illustrates the human inner ear with a direct simulation of vestibular nerve 42 via electrode 38 using signal receiving device 48. In the embodiment illustrated in FIG. 6, however, a pressure sensor 74 is provided in the nasopharynx 76 and communicates with signal receiving device 48 via a communication wire 78 that extends along the pharyngotympanic (auditory) tube 80, also referred to as the eustachian tube, between tympanic cavity 50 and nasopharynx 76. By being situated in the nasopharynx, pressure sensor 74 detects pressure changes in the patient resulting from respiration, upper airway dysfunction and swallowing. Of particular interest is detecting pressure changes resulting from respiration, so that the output from the sensor can be used as an input signal to trigger the vestibular stimulation.

Figure 6:
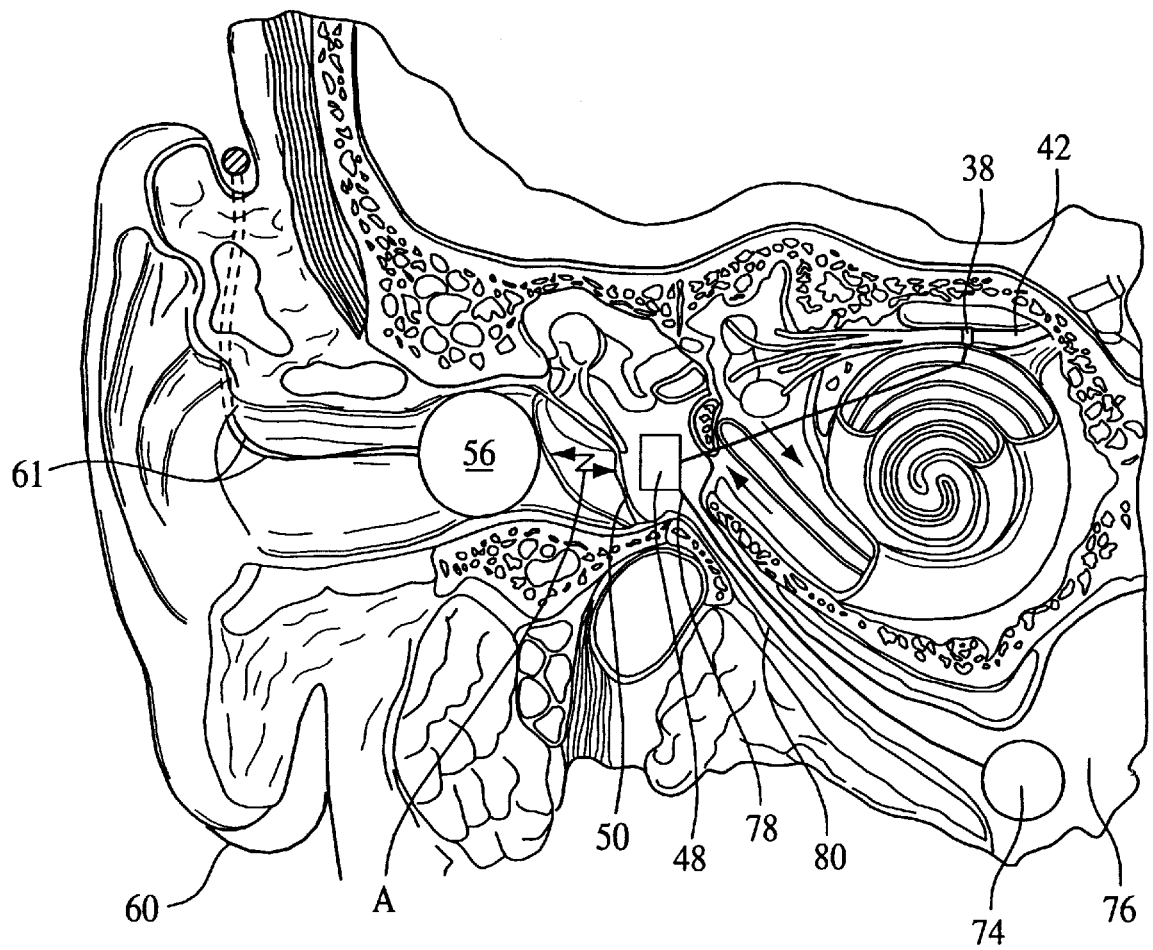
FIG. 6 is a sectional view of a portion of the human anatomy showing the inner ear and schematically showing a vestibular stimulation system with a sensor provided in the patient's nasopharynx according to a further embodiment of the present invention.

While FIG. 6 illustrates pressure sensor 74 as being provided in the nasopharynx, it is to be understood that the pressure sensor could be provided at other locations, such in the pharyngotympanic, so long as the sensor detects pressure changes in the upper airway region. In addition, other types of sensors in addition to or in place of pressure sensor 74 can be provided in communication with the patient's upper airway via the eustachian tube. For example, a microphone can be provided to detect respiration and/or snoring. In addition, the sensor or sensors in the nasopharynx and/or eustachian tube can communicate with another device, such as signal receiving device 48, wirelessly.

In one variation of this embodiment, signal receiving device 48 communicates with signal generating device 56, as indicated by arrow A, to transmit information regarding patient respiration from signal receiving device 48 to signal generating device 56, which is based on the output from pressure sensor 74, so that power/control unit 60 provides the appropriately time stimulation energy to the vestibular system. Another variation of this embodiment contemplates that the signal receiving device itself controls the application of stimulation energy to the vestibular system based on the output from pressure sensor 74. In which case, a constant supply of stimulation energy is preferably delivered by signal generating device 56 to signal receiving device 48 so that stimulation energy is always available when signal receiving device 48 determines that stimulation is to be applied.

In the embodiment shown in FIG. 6, power/control unit 60 is preferably worn behind the ear, with a lead 61 coupling the power/control unit to signal generating device 56 much in the same way a number of types hearing aids are currently used. It is to be understood, however, that the present invention contemplates locating power/control unit 60 anywhere on or near the patient so long as it functions for its intended purpose of providing a controlled supply of stimulation energy to the stimulation element(s).

While FIGS. 3 and 6 shows lead 54 as apparently passing through the cochlea, it is to be understood that this is preferably not the case. Lead 54 is shown overlying the cochlea for ease of illustration. Preferably, lead 54 is directed in a path from signal receiving device 48 to the stimulation electrode that minimizes damage to the patient's tissues.

Figure 7:
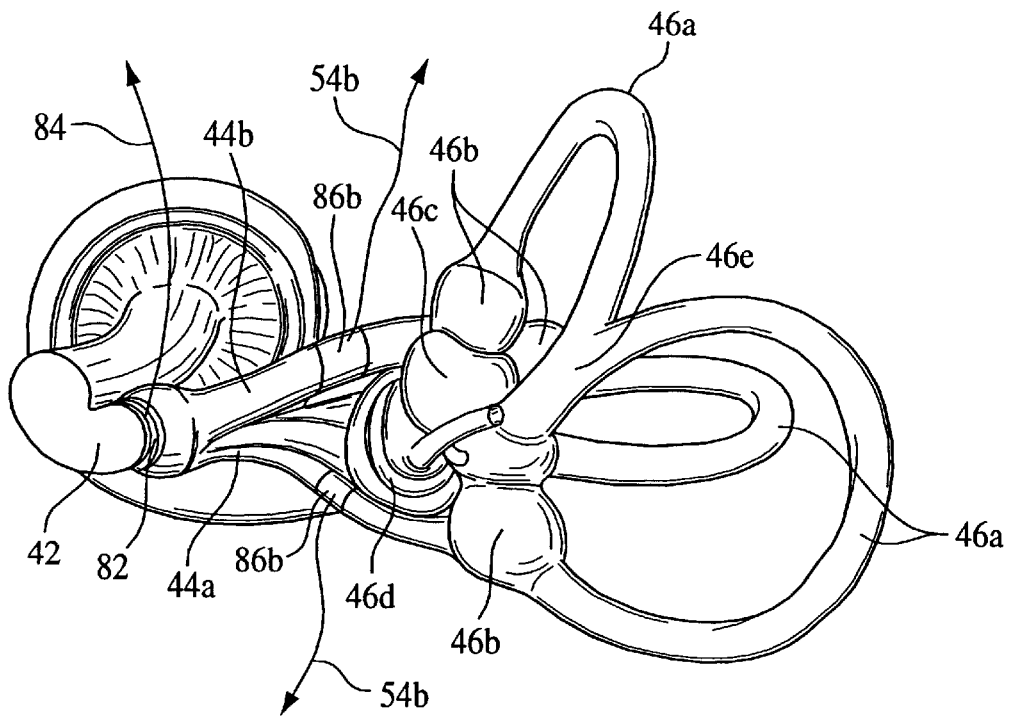
FIG. 7 is a posteromedial view of the labyrinth and associated nerves showing stimulation sites for augmenting/controlling the patient's respiration according to the principles of the present invention.

FIG. 7 is a posteromedial view of the labyrinth and associated nerves showing presently preferred stimulation sites according to the principles of the present invention for this embodiment. In this embodiment, augmenting the respiratory function is accomplished by inducing stimulation of the vestibular nerve so that the polysynaptic interaction of the vestibular nerve with the nerves associated with respiration can augment the patient's respiratory function. Thus, a primary function of the vestibular stimulation system is to induce a stimulation of the vestibular nerve. This is accomplished according to an exemplary embodiment of the present invention, as shown in FIG. 7, by stimulating vestibular nerve 42 directly and/or by stimulating one or more of nerve branches 44a and 44b. For example, an electrode 82 in direct contact with vestibular nerve provides the stimulation to this nerve. A lead 84 couples the electrode to the source of stimulation energy. Of course, lead 84 can be eliminated if stimulation energy is induced by the electrode itself, for example, by using a microstimulator as electrode 82, which is powered and controlled by an rf coupling. In addition, stimulation can be provided noninvasively, i.e., without lead 84 or electrode 82, using, for example, magnetic stimulation, in which a time-varying magnetic field is generated that creates a spatially varying electric field gradient to induce stimulation of the target area. Alternatively, or in addition to electrode 82, the present invention contemplates providing electrodes 86a and 86b in contact with nerve branches 44a and 44b, respectively, to stimulate the nerve branches, which, in turn, induce stimulation in the vestibular nerve. Leads 54a and 54b couple electrode 86a and 86b to the source of stimulation energy. Of course these leads can be eliminated as discussed above with respect to lead 84.

It is to be understood that the physiological function of augmenting the respiratory function of this embodiment of the present invention contemplate stimulating portions of the vestibular system before the vestibular nerve or nerve branches to induce a neural transmission therein. Thus, this embodiment of the present invention also contemplates stimulating the structures of the vestibular system, such as the semicircular canals 46a, ampullae 46b, utricle 46c, saccule 46d, and common membranous limb 46e using any of the above-described stimulation mechanisms. In addition, the present invention contemplates globally stimulating the vestibular area in synchronization with breathing to augment the patient's respiratory function.

In the above embodiment of the present invention, the vestibular system is used to augment the patient's respiratory function by in effect "boosting" the stimulation of the respiratory muscles via a stimulation applied to or induced in the vestibular nerve. In one embodiment of the present invention, this includes sensing the patient's respiration and appropriately timing the application of the stimulation energy to coincide with the respiratory cycle of the patient. However, as noted above, the present invention also contemplates controlling the patient's ventilation based on stimulation of the vestibular system. For example, instead of augmenting whatever respiratory function the patient may have, the stimulation system of the present invention takes over the responsibility of initiating or inducing inspiration. Such a system is particularly suited for patients suffering from central sleep apnea. For example, the present invention contemplates monitoring the patient's respiration, and once a cessation of breathing for a predetermined period of time is detected, vestibular stimulation is applied to induce or initiate inspiration.

In addition, the present invention contemplates providing appropriate alarms and other monitoring functions to monitor the patient an/or the condition of the stimulation system and communicate the monitored information to a caregiver and/or to a storage device, so that emergency conditions, such as failure of the vestibular stimulation system can be detected and reported. In addition, information on the use and function of the stimulation system can be obtained and recorded.

Maintaining Airway Patency

It is generally understood that relaxation of the muscles associated with the upper airway, such as the genioglossus, is a contributing factor, if not a primary factor, in the occurrence of obstructive sleep apnea for many individuals. It as also been found that tensing these upper airway muscles, at least during the inspiratory phase of the respiratory cycle, minimizes collapse of the upper airway. Thus, a further embodiment of the present invention contemplates reducing or minimizing the occurrence of OSA or upper airway resistance by tensing the upper airway muscles during at least the inspiratory phase of the respiratory cycle. It can be appreciated that because stimulation of the vestibular nerve elicits firing of the hypoglossal nerve and the recurrent laryngeal nerve, which are the primary nerves associated with the muscle groups in the upper airway, stimulating the vestibular nerve also tenses the upper airway muscles, thereby minimizing collapse of the upper airway. Thus, the present invention contemplates stimulating the vestibular system to minimizing collapse of the upper airway.

Preferably, stimulating the vestibular nerve to maintain airway patency is done in the manner discussed above with respect to stimulating this nerve to augment the patient's respiratory function, e.g., by stimulating the nerve directly or by stimulating tissues or nerve branches before the vestibular nerve, and using any of the stimulation techniques and mechanisms discussed above. In addition, stimulation is preferably synchronized with the inspiratory phase of the respiratory cycle, because it is during this phase that the negative pressure in the airway tends to urge the unsupported or undersupported airway to collapse. Therefore, the control systems and techniques discussed above are equally applicable to the use of the vestibular stimulation system for maintaining airway patency.

The present invention contemplates initiating the stimulation therapy to maintain airway patency based on an event, such as when the patient activates the therapy system or when the patient lies down to sleep, based on a timer, such as initiating the therapy at a set time period each night or some duration after the patient initiates a start of therapy or upon going to sleep. Once initiated, the stimulation therapy can be provided throughout the night. However, the present invention also contemplates providing the stimulation therapy to maintain airway patency only if conditions suggest that the patient is experiencing or likely to be experiencing an apnea or even a hypopnea. For example, the present invention contemplates initiating the stimulation therapy once it is determined that the patient is experiencing and apnea. This can be done using any conventional technique, such as by monitoring respiration (respiratory movement of the patient), respiratory flow, and/or oxygen saturation. The present invention also contemplates using snore to begin the stimulation therapy.

In addition, the present invention contemplates controlling the stimulation energy based on the severity of the patient's condition. For example, if apneas and/or snoring continue even after the stimulation therapy begins, the present invention contemplates increasing the stimulation level. Conversely, if apneas and/or snoring diminish, the stimulation level is reduced.

Preferably, stimulation energy is provided to the vestibular system prior to the onset of inspiration so that the muscles associated with the upper airway are contracting or beginning to contract before the inspiratory force increases to a level that would otherwise cause the upper airway to collapse. One reason for providing stimulation before the start of inspiration is to counteract the collapsing forces that act on the upper airway during inspiration. For example, once inspiration commences, a negative pressure is developed in the airway. This negative pressure tends to cause the airway to collapse or reduce in cross sectional area. It is believed that once the airway has collapsed, it is difficult, if not impossible, to overcome the collapsing forces.

In addition, to prevent airway collapse in the first place, it is believed to be preferable to make the cross-sectional area of the airway as large as possible before inspiratory flow begins in the airway. It can be appreciated that a reduction in the cross-sectional area of the airway increases the resistance to inspiratory flow, which, in turn, increases the negative pressure in the airway that urges the airway to collapse. If vestibular stimulation is applied prior to inspiration, the muscles associated with the airway are tensed, thereby preventing a reduction in the cross-sectional area to minimize the resistance to air flow. Minimizing the resistance to airflow improves airflow, thereby reducing negative pressure that potentially causes the airway to collapse. For these reasons, the present invention induces contraction in the muscles associated with the upper airway before a collapsing force, such as the negative pressure developed during inspiration, has the opportunity to cause the airway to collapse.

As noted above, in some patients, once a collapse or reduction in the airway has taken place, it is relatively difficult to open the airway by inducing contraction in the upper airway muscles. It is postulated that once airway collapse has occurred, the amount of tissue mass that must be moved is prohibitively large. In addition, if the patient is lying down, gravity tends to urge the tissues to collapse into the airway, so that opening the airway also requires overcoming the effects of gravity. Also, the action of the respiratory muscles in attempting to continue respiration may cause a vacuum to be created that tends to urge the airway tissues together, thereby making it especially difficult for an electrically induced contraction to be effective in opening the airway. Furthermore, the mucus-like characteristics of airway may cause a sealing effect, that also makes it especially difficult for an electrically induced contraction to be effective in opening the airway. Therefore, it is preferably to initiate stimulation prior to the onset of inspiration.

A primary difference between using the vestibular stimulation system of the present invention to augment or control the patient's respiratory effort and using the vestibular stimulation system to maintain airway patency is that the latter physiological function of maintaining airway patency is accomplished on an otherwise healthy patient that does not need ventilatory assistance. That is, the same basic system that monitors the respiratory cycles of a patient and stimulates the vestibular system in synchronization with the respiratory cycle can be used to either 1) augment the respiratory function if the patient requires ventilatory assistance or 2) maintain the opening of the airway if the patient suffers from OSA or upper airway resistance syndrome (UARS). Of course, both functions are accomplished if the patient suffers from OSA or UARS and requires ventilatory assistance.

Controlling/Pacing Respiration

The present invention also contemplates that the amount of stimulation applied to the vestibular system can be varied to control the force and duration of the inspiratory or expiratory effort. For example, it is known that taking a deep sigh once in a while is beneficial to respiration. Thus, the vestibular stimulation system of the present invention can be used on induce a deep sigh during the inspiratory phase of the respiratory cycle.

As noted above, the present invention contemplates that the power/control system can provide stimulation to the patient to serve as a diaphragm pacing device. For example, in some patients the ability to accurately and reliably trigger the respiratory cycle may be degraded or lost. Stimulating the vestibular nerve, either directly or indirectly, because it elicits a direct response in the phrenic nerve can be used to start and/or control the patient's inspiration. This embodiment is similar to the use of the vestibular stimulating system to treat central sleep apnea, where the stimulation device provides stimulation to the vestibular system if the patient has not initiated inspiration on their own after a certain amount of time elapses.

It can be appreciated that controlling the patient's ventilation requires providing timing logic in power/control unit 60 so that the stimulation energy is provided to the vestibular system in a cyclical fashion and so that the stimulation energy is provided for the proper duration. It is to be understood that the power/control unit can be programmed to vary the pattern for the patient's respiratory cycle randomly, which is known to enhance the ventilation function. It is to be further understood that the techniques that are used to control conventional electroventilation device can be used to control the vestibular stimulation system of the present embodiment. The difference being that, in the present invention, the electrical stimulation is provided to the vestibular system to accomplish the macro stimulation of many, if not all, of the neural-muscular systems associated with respiration, rather than one specific component thereof, such as stimulating the diaphragm.

Inducing or Promoting Sleep

A further embodiment of the present invention contemplates providing stimulation to the appropriate portions of the vestibular system in an appropriately timed fashion so as to produce the sensation of rocking in the patient. It is believed that this rocking sensation produced from an artificial stimulation of the vestibular system, just as with physically rocking the patient, will induce sleep in the patient and, for a sleeping patient, will promote a more restful sleep.

Figure 8:
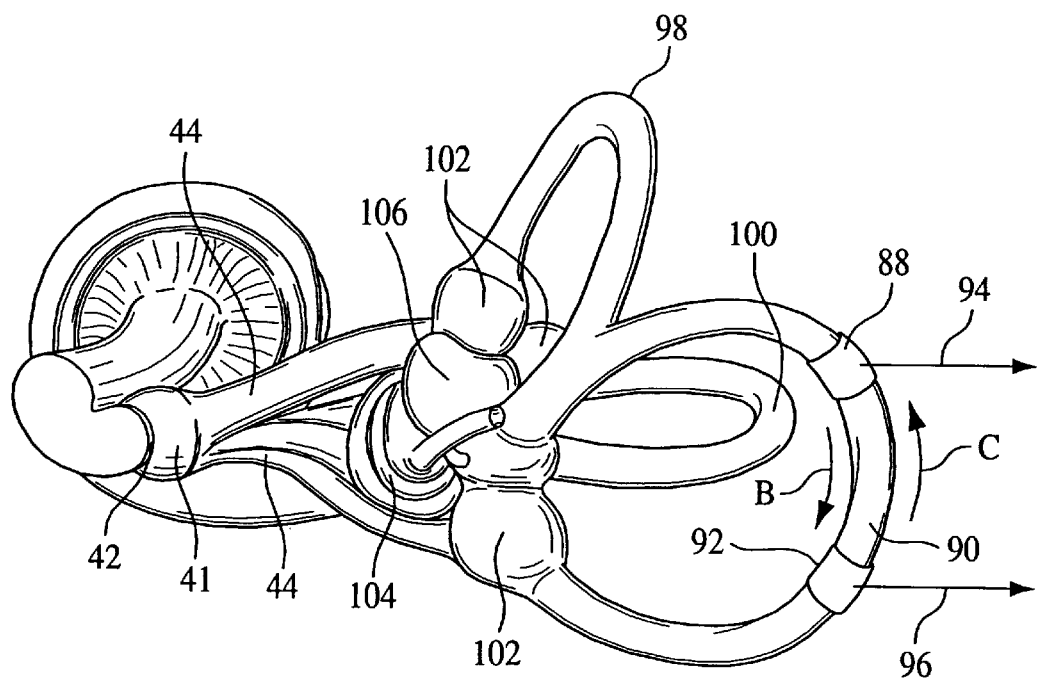
FIG. 8 is another posteromedial view of the labyrinth and associated nerves showing stimulation sites for inducing sleep according to the principles of the present invention.

In one embodiment of the present invention, the sensation of rocking is induced by stimulating one or more the semicircular canals, saccules, and/or utricles. For example, FIG. 8 illustrates a first stimulation element 88 provided at a first location on semicircular canal 90 and a second stimulation element 92 provided at a second location on the same semicircular canal. First and second stimulation elements 88 and 92 are operatively coupled to a signal receiving device for controlling the application of stimulation to semicircular canal 90. In one embodiment, stimulation elements 88 and 92 are electrodes, such as cuff electrodes discussed above, for providing electrical energy to the patient from a source. Leads 94 and 96 couple the electrodes to the power supply. In another embodiment, first and second stimulation elements 88 and 92 are pressure application devices, such as the pressure cuffs discussed above, that apply a pressure to the semicircular canal. In which case, leads 94 and 96 are conduits for carrying an inflating fluid to the pressure cuffs. In yet another embodiment, first and second stimulation elements 88 and 92 are pressure application devices located within the semicircular canal for moving the fluid contained therein. In still another embodiment of the present invention, stimulation of the canals is accomplished via one or more vibrating elements located proximate to the semicircular canal, such as in the bone tissue adjacent the duct in which the semicircular canal is located.

In this embodiment, a rocking sensation is induced in the patient by alternatively actuating first and second stimulation elements 88 and 92. For example, if first and second stimulation elements 88 and 92 are pressure cuffs, first stimulation element 88 is actuated and second stimulation element 92 is deactivated to tend to urge the fluid within semicircular canal 90 in a first direction toward the second stimulation element, as indicated by arrow B. Thereafter, first stimulation element 88 is deactivated and second stimulation element 92 is actuated to urge the fluid in the opposite direction back toward the first stimulation element, as indicated by arrow C. This process can be repeated to move the fluid back and forth within the semicircular canal, which is the same effect that takes place when the person is physically rocked. Of course, the frequency of the back and forth movement of the fluid can be altered to change the rocking speed of the patient.

It is to be understood, that the placement of first and second stimulation element 88 and 92 on semicircular canal 90, which is the posterior semicircular canal, may not be the optimum location for all patients. Thus, the present invention contemplates locating the first and second stimulation element on other semicircular canals, such as anterior semicircular canal 98 and/or lateral semicircular canal 100. It is to be understood that such stimulation elements can be provided at one or more of these semicircular canals, which is especially important given the three-dimensional nature of the human balancing system. It is to be further understood that the number of stimulation elements and their specific location on the associated semicircular canals is also subject to variation so long as the actuation of these stimulation elements produces a rocking sensation in the patient.

In another embodiment of the present invention, the stimulation elements are provided at ampullae 102, saccule 104, and/or utricle 106 rather than on, in or adjacent to the semicircular canals. The present invention contemplates using the stimulation techniques discussed above with respect to FIG. 8 to alternatively stimulate these structures to create a rocking sensation.

Because one object of this embodiment of the present invention is to simulate rocking for the purpose of inducing sleep, a further variation of this embodiment of the present invention contemplates detecting when the patient has fallen asleep and automatically discontinuing the rocking type stimulation. The present invention contemplates using any one of the variety of known techniques to detect when the patient is asleep. The rocking type stimulation can then be decreased immediately once sleep is detected or, preferably, gradually, so as not to arouse the patient from sleep. The present invention also contemplates discontinuing the rocking type stimulation after a set duration, such as a predetermined period of time, following initiation of the stimulation therapy. Such a stimulation would include a timer, for example, to monitor the amount of time since the stimulation began or the amount of time remaining until stimulation is to be discontinued. This embodiment of the present invention allows the rocking type stimulation is applied to put the patient to sleep, and discontinues the stimulation some time later, preferably once the patient has fallen asleep, much the same way a sleep timer functions on a radio or television. Of course, the rocking type stimulation can continue even after the patient has fallen asleep. It is believed that stimulating a sleeping patient in this fashion helps promote a more restful sleep.

Inducing a rocking sensation in the patient can also be done non-invasively, using a vestibular stimulation system similar to that shown in FIG. 2. In this embodiment a first stimulating electrode is located on the surface of the patient proximate to a left vestibular system of a patient, and a second stimulating electrode is disposed proximate to a right vestibular system of a patient. The control unit applies stimulation energy having an alternating polarity between the first and the second electrodes to induce the rocking sensation. This is accomplished by providing, for example, a sinusoidal voltage waveform between the first and second stimulating electrodes to alternate the polarity of the current stimulating the patient's vestibular systems.

It should be noted that the term "rocking" as used herein is not intended to be limited to a back and forth, i.e., posterior to anterior and anterior to posterior motion, as is the conventional meaning of this term. On the contrary, the sensation of rocking also refers to the sensation of side to side, lateral or a swaying movement, as well as a combination of back and forth and sided to side motion, which can be considered a circular motion.

Counteracting Vertigo

A still further embodiment of the present invention contemplates providing stimulation to the appropriate portions of the vestibular system in an appropriately timed fashion so as to counteract dizziness and/or vertigo, which is the sensation that the patient's surroundings are whirling. Vertigo is the result of the vestibular system outputting neurological signals according to a firing pattern that the brain recognizes as a spinning sensation. Vertigo is not necessarily the result of physically spinning the patient. However, dizziness may result from such physical spinning.

The present invention contemplates counteracting vertigo and/or dizziness by stimulating the vestibular system in an offsetting fashion to, in effect, mask out or block the neural transmissions that the brain would otherwise interpret as dizziness or a vertigo sensation. For example, suppose that the patient has the sensation that they are spinning to the left, which is the result of the vestibular system outputting neural signals in a first pattern. The present invention contemplates stimulating the vestibular system or portions thereof so as prevent this first pattern from being provided to the brain or to alter the pattern being sent to the brain so that the brain no longer senses that the person is spinning. For example, if the firing frequency of the neurons slows down when the patient is spinning, thereby signaling the brain that the person is spinning, the stimulation system of the present invention can be used to increase the neuron firing frequency, thereby signaling the brain that the person is not spinning.

This "blocking" function can be accomplished whether or not the person is actually spinning. For example, if the patient suffers from a balance disorder, such as vertigo, the blocking function can be used to mask the signals from the vestibular system that cause the brain to think the patient is unbalanced even when they are not.

However, the present invention also contemplates providing stimulation to the vestibular system to counteract dizziness only if the patient is actually spinning. For example, the present invention contemplates providing an accelerometer as sensor 34 to detect acceleration or movement of the patient's head or body. If acceleration is detected, the vestibular system is stimulated in a manner so as to counteract the dizzy sensation. This embodiment for the vestibular stimulation system is particularly suited for applications where the user is likely to experience dizziness but needs to continue performing functions that may otherwise not be possible for someone experiencing vertigo. For example, a test pilot may experience vertigo if their plane enters a spin. The present invention contemplates that the stimulation system detects that the pilot is spinning and initiates vestibular stimulation to counteract the act the vertigo so that the pilot can attempt to regain control or eject, which are tasks that would otherwise be difficult it the pilot is experiencing vertigo.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A vestibular stimulation system comprising:

a power supply;

a stimulation element operatively coupled to the power supply and adapted to provide a stimulation energy to at least a portion of a vestibular system of a patient; and a control unit operatively coupled to at least one of the power supply and the stimulation element so as to control an application of the stimulation energy to at least a portion of a vestibular system of such a patient so as to induce a rocking sensation in such a patient.

2. A system according to claim 1, wherein the stimulation element is one of: an electrode, a mechanism that generates a mechanical motion as the stimulation energy, a sonic emitter, an ultrasonic emitter, a magnetic field generator, a thermal generating element, a chemical injector, an rf emitter and an infrared emitter.

3. A system according to claim 1, wherein the stimulation element is a surface electrode adapted to be disposed on a surface of such a patient's skull behind such a patient's ear.

4. A system according to claim 1, wherein the control unit controls a characteristic of the stimulation energy applied to at least a portion of a vestibular system of such a patient, including at least one of an amplitude, a waveform shape, a frequency, and a duration of the stimulation energy.

5. A system according to claim 1, wherein the stimulating element includes a first stimulating electrode disposed proximate to a left vestibular system of a patient, and a second stimulating electrode disposed proximate to a right vestibular system of a patient, and wherein the control unit applies an alternating polarity waveform between the first and the second electrodes to induce the rocking sensation.

6. A system according to claim 1, wherein the control unit terminates the application of the stimulation energy responsive to at least one of (1) an elapse of a predetermined period of time and (2) an occurrence of a predetermined event.

7. A vestibular stimulation system comprising:

stimulating means for providing a stimulation energy to at least a portion of a vestibular system of a patient; and controlling means for controlling an application of the stimulation energy to at least a portion of a vestibular system of such a patient so as to induce a rocking sensation in such a patient.

8. A system according to claim 7, further comprising positioning means for locating the stimulating means proximate to a vestibular system of a patient.

9. A system according to claim 7, wherein the controlling means also terminates the application of the stimulation energy responsive to at least one of (1) an elapse of a predetermined period of time and (2) an occurrence of a predetermined event.

10. A system according to claim 7, wherein the controlling means also controls a characteristic of the stimulation energy applied to at least a portion of a vestibular system of such a patient, including at least one of an amplitude, a waveform shape, a frequency, and a duration of the stimulation energy applied to a patient.

11. A vestibular stimulation method comprising:
providing a stimulation energy to at least a portion of a vestibular system of a patient; and
controlling an application of the stimulation energy to at least a portion of a vestibular system of such a patient so as to induce a rocking sensation in such a patient.

12. A method according to claim 11, wherein providing the stimulation energy includes locating a stimulation element proximate to a vestibular system of a patient.

13. A method according to claim 11, wherein providing the stimulation energy includes locating a first stimulating electrode proximate to a left vestibular system of a patient, and locating a second stimulating electrode disposed proximate to a right vestibular system of a patient, and wherein the controlling the application of stimulation energy includes providing an alternating polarity waveform between the first and the second electrodes to induce the rocking sensation.

14. A method according to claim 11, wherein controlling the application of stimulation energy includes termination the application of the stimulation energy responsive to at least one of (1) an elapse of a predetermined period of time and (2) an occurrence of a predetermined event.

15. A method according to claim 11, wherein controlling the application of stimulation energy includes controlling a characteristic of the stimulation energy applied to at least a portion of a vestibular system of such a patient, including at least one of an amplitude, a waveform shape, a frequency, and a duration of the stimulation energy applied to a patient.

16. A vestibular stimulation system comprising:
a power supply;
a stimulation element operatively coupled to the power supply and adapted to provide a stimulation energy to at least a portion of a vestibular system of a patient so as to induce contraction of such a patient's respiratory muscles; and
a control unit operatively coupled to at least one of the power supply and the stimulation element so as to control an application of the stimulation energy to at least a portion of a vestibular system of such a patient.

17. A system according to claim 16, wherein the control unit causes the stimulation element to deliver the stimulation energy in a continuous manner according to a predetermined pattern.

18. A system according to claim 16, wherein the control unit causes the stimulation element to deliver the stimulation energy in a manner so as to augment such a patient's respiratory effort.

19. A system according to claim 16, further comprising a sensor adapted to detect a physiological characteristic of such a patient and to output a signal indicative thereof to the control unit, and wherein the control unit controls the application of stimulation energy to such a patient based on the output of the sensor.

20. A system according to claim 19, wherein the sensor is adapted to detect a physiological characteristic associated with respiration, and wherein the control unit determines, from the signal from the sensor, whether such a patient is in one of an inspiratory phase and an expiratory phase of a breathing cycle, and controls the application of stimulation energy to a patient so that stimulation energy is provided at least during at least one of: (1) a period of time just prior to an onset of the inspiratory phase, (2) a period of time encompassing the onset of the inspiratory phase, and (3) a period of during the inspiratory phase following the onset of the inspiratory phase.

21. A system according to claim 16, wherein the control unit causes the stimulation element to deliver the stimulation energy in a manner so as to induce contraction of such a patient's upper airway muscles to maintain airway patency.

22. A system according to claim 21, further comprising a sensor adapted to detect a physiological characteristic of such a patient associated with respiration and to output a signal indicative thereof to the control unit, and wherein the control unit determines, from the signal from the sensor, whether such a patient is experiencing a breathing disorder, and controls the application of stimulation energy so that the stimulation energy is provided responsive to such a patient experiencing a breathing disorder.

23. A system according to claim 16, wherein the stimulation element is one of: an electrode, a mechanism that generates a mechanical motion as the stimulation energy, a sonic emitter, an ultrasonic emitter, a magnetic field generator, a thermal generating element, a chemical injector, an rf emitter and an infrared emitter.

24. A system according to claim 16, wherein the stimulation element is a surface electrode adapted to be disposed on a surface of such a patient's skull behind such a patient's ear.

25. A system according to claim 16, wherein the control unit controls a characteristic of the stimulation energy applied to at least a portion of a vestibular system of such a patient, including at least one of an amplitude, a waveform shape, a frequency, and a duration of the stimulation energy.

26. A vestibular stimulation system comprising:
stimulating means for providing a stimulation energy to at least a portion of a vestibular system of a patient so as to induce contraction of such a patient's respiratory muscles;
energy means for providing energy to power the stimulating means; and
controlling means, associated with at least one of the stimulating means and the energy means, for controlling an application of the stimulation energy to such a patient by the stimulating means.

27. A system according to claim 26, wherein the controlling means controls the application of the stimulation energy in a continuous manner according to a predetermined pattern.

28. A system according to claim 26, wherein the controlling means controls the application of the stimulation energy in a manner so as to augment such a patient's respiratory effort.

29. A system according to claim 26, further comprising a sensing means for detecting a physiological characteristic of such a patient, and wherein the controlling means controls the application of stimulation energy to such a patient based on an output of the sensing means.

30. A system according to claim 26, wherein the controlling means also controls a characteristic of the stimulation energy applied to at least a portion of a vestibular system of such a patient, including at least one of an amplitude, a waveform shape, a frequency, and a duration of the stimulation energy applied to a patient.

31. A system according to claim 26, further comprising positioning means for locating the stimulating means on a surface of such a patient's skull behind such a patient's ear.

32. A system according to claim 26, wherein the controlling means controls the application of the stimulation energy in a manner so as to induce contraction of such a patient's upper airway muscles to maintain airway patency.

33. A vestibular stimulation method comprising:
   providing a stimulation energy to at least a portion of a vestibular system of a patient so as to induce contraction of such a patient's respiratory muscles; and
   controlling the application of the stimulation energy to such a patient.

34. A method according to claim 33, wherein providing stimulation energy includes:
   locating a stimulating electrode proximate to a vestibular system of a patient; and
   providing electrical energy to the stimulating electrode from a power source.

35. A method according to claim 33, wherein controlling the application of the stimulation energy includes providing the stimulation energy in a continuous manner according to a predetermined pattern.

36. A method according to claim 33, wherein controlling the application of the stimulation energy includes providing the stimulation energy in a manner so as to augment such a patient's respiratory effort.

37. A method according to claim 33, further comprising detecting a physiological characteristic of such a patient, and wherein controlling the application of the stimulation energy is done based on an output of the detecting step.

38. A method according to claim 37, wherein detecting a physiological characteristic includes detecting a physiological characteristic associated with respiration, and further comprising determining, from the detected physiological characteristic associated with respiration, whether such a patient is in one of an inspiratory phase and an expiratory phase of a breathing cycle, and wherein controlling the application of stimulation energy includes applying the stimulation energy at least during at least one of: (1) a period of time just prior to an onset of the inspiratory phase, (2) a period of time encompassing the onset of the inspiratory phase, and (3) a period of during the inspiratory phase following the onset of the inspiratory phase.

39. A method according to claim 33, further comprising detecting a physiological characteristic of such a patient associated with respiration, further comprising determining, from the detected physiological characteristic associated with respiration, whether such a patient is experiencing a breathing disorder, and wherein controlling the application of stimulation energy includes applying the stimulation energy responsive to such a patient experiencing a breathing disorder.

40. A method according to claim 33, wherein controlling the application of the stimulation energy also includes controlling a characteristic of the stimulation energy applied to at least a portion of a vestibular system of such a patient, including controlling at least one of an amplitude, a waveform shape, a frequency, and a duration of the stimulation energy applied to such a patient.

* * * * *